United States Patent
Nishii et al.

(10) Patent No.: US 10,336,718 B2
(45) Date of Patent: Jul. 2, 2019

(54) METHOD FOR INDUSTRIAL PRODUCTION OF OPTICALLY ACTIVE FLUOROALKYL ETHYLENE OXIDE

(71) Applicant: Central Glass Company, Limited, Ube-shi, Yamaguchi (JP)

(72) Inventors: Tetsuro Nishii, Kawagoe (JP); Ayumi Yamaguchi, Kawagoe (JP); Takashi Ootsuka, Kawagoe (JP); Naoki Sawai, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/739,498

(22) PCT Filed: Jun. 24, 2016

(86) PCT No.: PCT/JP2016/068747
§ 371 (c)(1),
(2) Date: Jul. 20, 2018

(87) PCT Pub. No.: WO2016/208699
PCT Pub. Date: Dec. 29, 2016

(65) Prior Publication Data
US 2018/0312483 A1    Nov. 1, 2018

(30) Foreign Application Priority Data

Jun. 25, 2015 (JP) .................................. 2015-127909

(51) Int. Cl.
| | | |
|---|---|---|
| *C07D 307/89* | (2006.01) | |
| *C07D 301/26* | (2006.01) | |
| *C07C 29/143* | (2006.01) | |
| *C07C 31/34* | (2006.01) | |
| *C07B 53/00* | (2006.01) | |
| *C07D 303/08* | (2006.01) | |
| *C12P 7/04* | (2006.01) | |
| *C07C 31/42* | (2006.01) | |
| *C07C 29/10* | (2006.01) | |
| *C12R 1/72* | (2006.01) | |
| *C12R 1/645* | (2006.01) | |

(52) U.S. Cl.
CPC ............ *C07D 301/26* (2013.01); *C07B 53/00* (2013.01); *C07C 29/106* (2013.01); *C07C 29/143* (2013.01); *C07C 31/34* (2013.01); *C07C 31/42* (2013.01); *C07D 303/08* (2013.01); *C12P 7/04* (2013.01); *C12Y 101/01001* (2013.01); *C12Y 101/01184* (2013.01); *C12R 1/645* (2013.01); *C12R 1/72* (2013.01); *Y02P 20/582* (2015.11)

(58) Field of Classification Search
CPC .. C07D 301/26; C07D 303/08; C07C 29/143; C07C 31/34; C12P 7/04

USPC ........................................................ 549/251
See application file for complete search history.

(56) References Cited

U.S. PATENT DOCUMENTS

| | | | |
|---|---|---|---|
| 2,700,686 | A | 1/1955 | Dickey et al. |
| 2,746,952 | A | 5/1956 | Dickey et al. |
| 2009/0203096 | A1 | 8/2009 | Hayashi et al. |
| 2013/0005007 | A1 | 1/2013 | Asano et al. |
| 2016/0138059 | A1 | 5/2016 | Sawai et al. |

FOREIGN PATENT DOCUMENTS

| | | | |
|---|---|---|---|
| JP | | 6-247953 A | 9/1994 |
| JP | | 10-279571 A | 10/1998 |
| JP | | 2006-328011 A | 12/2006 |
| JP | | 2009-514542 A | 4/2009 |
| JP | | 2012-5396 A | 1/2012 |
| WO | WO 2006/058457 A1 | | 6/2006 |
| WO | WO 2007/054411 A1 | | 5/2007 |
| WO | WO 2007/142210 A1 | | 12/2007 |
| WO | WO 2011/099595 A1 | | 8/2011 |
| WO | WO 2015/005341 A1 | | 1/2015 |

OTHER PUBLICATIONS

International Search Report (PCT/ISA/210) issued in PCT Application No. PCT/JP2016/068747 dated Aug. 9, 2016 with English translation (five pages).
Japanese-language Written Opinion (PCT/ISA/237) issued in PCT Application No. PCT/JP2016/068747 dated Aug. 9, 2016 (four pages).
K. Furuhashi, "Biological Routes to Optically Active Epoxides," Chirality in Industry, 1992, pp. 167-186, John Wiley & Sons Ltd, New York.
Schaus, et al., "Highly Selective Hydrolytic Kinetic Resolution of Terminal Epoxides Catalyzed by Chiral (salen) $Co^{III}$ Complexes. Practical Synthesis of Enantioenriched Terminal Epoxides and 1,2-Diols," Journal of the American Chemical Society, 2002, pp. 1307-1315, vol. 124, No. 7, United States.
Ramachandran, et al., "Chiral Synthesis via Organoboranes. 40. Selective Reductions. 55. A Simple One-Pot Synthesis of Enantiomers of (Trifluoromethyl)oxirane. A General Synthesis of High Optical Purities of α-Trifluoromethyl Secondary Alcohols via the Ring-Cleavage Reactions of the Epoxide," J. Org. Chem, 1995, pp. 41-46, vol. 60, American Chemical Society, United States.

(Continued)

*Primary Examiner* — Taylor V Oh
(74) *Attorney, Agent, or Firm* — Crowell & Moring LLP

(57) ABSTRACT

It is possible to produce an optically active fluoroalkyl chloromethyl alcohol with a high optical purity and a good yield by treating a fluoroalkyl chloromethyl ketone with a microorganism having an activity for asymmetrically reducing the ketone or an enzyme having the activity. Then, it is possible to obtain a fluoroalkyl ethylene oxide by treating the alcohol with a base. Industrial implementation of the production method of the present invention is easy.

16 Claims, No Drawings

(56) References Cited

OTHER PUBLICATIONS

Bussche-Hunnefeld, et al., "Ergiebige Herstellung von (R)- und (S)-3,3,3,-Trifluormilchsäure und von (R)- and (S)-(Trifluoromethyl)oxiran," Chem. Ber., 1992, pp. 2795-2802, vol. 125.

METHOD FOR INDUSTRIAL PRODUCTION OF OPTICALLY ACTIVE FLUOROALKYL ETHYLENE OXIDE

TECHNICAL FIELD

The present invention relates to a method for industrial production of an optically active fluoroalkyl ethylene oxide.

BACKGROUND TECHNOLOGY

Optically active fluoroalkyl ethylene oxides are important compounds as various medicinal and agricultural chemical intermediates. As methods for producing optically active 2-trifluoromethyl ethylene oxide, Non-patent Publication 1 discloses a method by an asymmetrical oxidation of 1,1,1-trifluoropropene using microorganism, Non-patent Publication 2 discloses a method by a kinetic optical resolution of racemic 2-trifluoromethyl ethylene oxide, Non-patent Publication 3 discloses a method in which 3-bromo-1,1,1-trifluoro-2-propanone is asymmetrically reduced by an asymmetric reducing agent, and the obtained optically active 1-bromo-3,3,3-trifluoroisopropyl alcohol is treated with base to achieve a ring closure, Non-patent Publication 4 discloses a method in which optically active 3,3,3-trifluorolactic acid is obtained by using an optical resolution agent, and a sulfonic acid ester obtained by conducting a multistep procedure, such as protecting the substituent with a protecting group, deprotecting, esterification, etc., is treated with base, and Patent Publication 1 discloses a method in which optically active 3,3,3-trifluoro-1,2-propanediol is increased by recrystallization in optical purity, followed by conversion into optically active 1-chloro-3,3,3-trifluoroisopropyl alcohol and then treatment with base to achieve a ring closure.

Meanwhile, the present inventors disclose in Patent Publication 2 a method in which optically active 3,3,3-trifluorolactic acid is converted into optically active 3,3,3-trifluoro-1,2-propanediol, followed by conversion into a halohydrin through a cyclic sulfuric acid ester and then into optically active 2-trifluoromethyl ethylene oxide.

Furthermore, as to optically active 2-monofluoromethyl ethylene oxide, Non-patent Publication 2 discloses a method by a kinetic optical resolution of racemic 2-monofluoromethyl ethylene oxide.

On the other hand, no synthesis example of optically active 2-difluoromethyl ethylene oxide has been known so far.

PRIOR ART PUBLICATIONS

Patent Publications

Patent Publication 1: JP Patent Application Publication H6-247953
Patent Publication 2: JP Patent Application Publication 2006-328011

Non-Patent Publications

Non-patent Publication 1: Chirality in Industry, Wiley, New York, 1992
Non-patent Publication 2: S. E. Schaus, B. D. Brandes, J. F. Larrow, M. Tokunaga, B. Hansen, A. E. Gould, M. E. Furrow, and E. N. Jacobsen, Journal of the American Chemical Society, 2002, 124, 1307-1315
Non-patent Publication 3: P. V. Ramachandran, B. Gong, H. C. Brown, J. Org. Chem, 1995, 60, 41-46
Non-patent Publication 4: C. von dem Bussche-Hunnefeld, C. Cescato, D. Seebach, Chem. Ber., 1992, 125, 2795-2802

SUMMARY OF THE INVENTION

Task to be Solved by the Invention

As mentioned above, as to 2-trifluoromethyl ethylene oxide, Non-patent Publication 1 discloses a method by an asymmetrical oxidation of 1,1,1-trifluoropropene by microorganism. Although it shows applicability of a biological asymmetrical oxidation, it was possible to produce only an S-form enantiomer. Non-patent Publication 2 discloses a method by a kinetic optical resolution of racemic 2-trifluoromethyl ethylene oxide using a chemical catalyst. It discloses that optically active 2-trifluoromethyl ethylene oxide having an extremely high optical purity of 99% ee or greater is obtained. However, when conducting optical resolution again by using 2-trifluoromethyl ethylene oxide with an undesirable stereochemistry, there was difficulty in the operation. That is, it is extremely difficult to convert 3,3,3-trifluoro-1,2-propanediol, resulting from hydrolysis of 2-trifluoromethyl ethylene oxide, into a precursor of 2-trifluoromethyl ethylene oxide having racemic form or the target stereochemistry. As a result, it is not possible to expect optically active 2-trifluoromethyl ethylene oxide having the target stereochemistry to achieve a yield of 50% or greater. Therefore, its industrial adaptation was difficult. Non-patent Publication 3 discloses a method by an asymmetric reduction of 3-bromo-1,1,1-trifluoro-2-propanone using an asymmetric reducing agent to obtain optically active 2-trifluoromethyl ethylene oxide through optically active 1-bromo-3,3,3-trifluoroisopropyl alcohol having a high optical purity of 96% ee. It is, however, necessary to stoichiometrically use a high-price asymmetrical reducing agent. Therefore, it was not an industrial method. Non-patent Publication 4 discloses a method of obtaining 2-trifluoromethyl ethylene oxide from optically active 3,3,3-trifluorolactic acid. However, not only the reaction is cumbersome due to its multistep procedure, but also theoretical yield is 50% at most. Therefore, it was not an industrial method.

Patent Publication 1 discloses a method in which optically active 3,3,3-trifluoro-1,2-propanediol obtained by various methods is converted into 1-chloro-3,3,3-trifluoroisopropyl alcohol, followed by conducting a ring closure by base. However, there was a problem of low yield.

The task of the present invention is to provide a method for industrially producing an optically active fluoroalkyl ethylene oxide.

Means for Solving the Task

As a result of an eager study, the present inventors have found a method in which a fluoroalkyl chloromethyl ketone is treated with a particular biocatalyst (microorganism or enzyme) to make an asymmetrical reduction proceed efficiently and to obtain an optically active fluoroalkyl chloromethyl alcohol with a high stereoselectivity. Furthermore, we have obtained findings to convert the alcohol to a fluoroalkyl ethylene oxide with a high yield, while maintaining optical purity, thereby completing the present invention.

That is, the present invention provides inventions described in the following [Invention 1] to [Invention 17].

[Invention 1]

A method for producing an optically active fluoroalkyl chloromethyl alcohol represented by formula [2]:

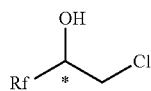

[2]

[In the formula, * represents an asymmetric atom, and Rf is defined as in formula [1].]

the method comprising the step of treating a fluoroalkyl chloromethyl ketone represented by formula [1]:

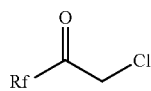

[1]

[In the formula, Rf represents a $C_{1-6}$ straight-chain or branched-chain fluoroalkyl group having at least one fluorine atom.]

with a microorganism having an activity for asymmetrically reducing the ketone or an enzyme having the activity.

[Invention 2]

The production method as mentioned in Invention 1, wherein Rf in the fluoroalkyl chloromethyl ketone represented by formula [1] is a trifluoromethyl ($CF_3$) group or difluoromethyl ($CF_2H$) group.

[Invention 3]

The production method as mentioned in Invention 1 or 2, wherein the microorganism is at least one selected from the group consisting of *Cryptococcus curvatus*, *Pichia farinosa*, *Torulaspora delbrueckii*, *Candida cacaoi*, *Rhodotorula mucilaginosa*, *Sporidibolus johnsonii*, and *Trichosporon cutaneum*.

[Invention 4]

The production method as mentioned in Invention 3, which is characterized in that the microorganism is a microorganism having a deposit number shown in the following.

TABLE 1

| Microorganism | Deposit number | Depositary |
|---|---|---|
| *Cryptococcus curvatus* | NBRC 1159 | National Institute of Technology and Evaluation |
| *Pichia farinosa* | NBRC 0462 | National Institute of Technology and Evaluation |
| *Torulaspora delbrueckii* | NBRC 0381 | National Institute of Technology and Evaluation |
| *Candida cacaoi* | NBRC 10231 | National Institute of Technology and Evaluation |
| *Rhodotorula mucilaginosa* | NBRC 0001 | National Institute of Technology and Evaluation |
| *Sporidibolus johnsonii* | NBRC 6903 | National Institute of Technology and Evaluation |
| *Trichosporon cutaneum* | NBRC 1198 | National Institute of Technology and Evaluation |

[Invention 5]

The production method as mentioned in Invention 1, which is characterized in that the enzyme is an alcohol dehydrogenase or carbonyl reductase.

[Invention 6]

The production method as mentioned in Invention 5, which is characterized in that the alcohol dehydrogenase or carbonyl reductase is a microorganism of Tremellaceae, Saccharomycetaceae, *Rhodotorula*, *Sporidibolus* or Trichosporonaceae, a substance treated therewith, a culture thereof, and/or an enzyme obtained from the microorganism.

[Invention 7]

The production method as mentioned in any of Inventions 1 to 6, which is characterized in that temperature in the reaction (reaction temperature) is 5 to 60° C.

[Invention 8]

The production method as mentioned in any of Inventions 1 to 7, which is characterized in that pH in the reaction (pH at a time of the reaction) is in a range of 4.0 to 8.0.

[Invention 9]

The production method as mentioned in any of Inventions 1 to 8, comprising the step of distilling a mixed liquid containing the optically active fluoroalcohol obtained after terminating the reaction and an impurity, thereby separating the impurity from the mixed liquid and purifying the optically active fluoroalcohol.

[Invention 10]

A method for producing an optically active fluoroalkyl ethylene oxide represented by formula [3]:

[3]

[In the formula, * represents an asymmetric atom, and Rf is defined as in formula [1] in claim 1.]

the method being characterized in that the optically active fluoroalkyl chloromethyl alcohol represented by formula [2] is produced by the method of any of Inventions 1 to 9, and then the alcohol is treated with a base.

[Invention 11]

The production method as mentioned in Invention 10, wherein the base is at least one selected from the group consisting of alkali metal hydrides, alkali-earth metal hydrides, alkali metal hydroxides, alkali-earth metal hydroxides, alkali metal carbonates, alkali-earth metal carbonates, alkali metal hydrogencarbonates, and alkali-earth metal hydrogencarbonates.

[Invention 12]

The production method as mentioned in Invention 10 or Invention 11, further comprising the step of hydrolyzing the optically active fluoroalkyl ethylene oxide, thereby turning into a fluoroalkyl-1,2-ethanediol represented by formula [4]:

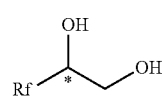

[4]

[In the formula, * represents an asymmetric atom, and Rf is defined as in formula [1] in claim 1.].

[Invention 13]

The method as mentioned in Invention 12, wherein the hydrolysis is conducted by a treatment with an acid or base.

[Invention 14]

The method as mentioned in Invention 13, wherein the base is at least one selected from the group consisting of alkali metal hydrides, alkali-earth metal hydrides, alkali metal hydroxides, alkali-earth metal hydroxides, alkali metal carbonates, alkali-earth metal carbonates, alkali metal hydrogencarbonates, and alkali-earth metal hydrogencarbonates.

[Invention 15]

The production method as mentioned in any of Inventions 12 to 14, wherein the step of turning into the fluoroalkyl-1,2-ethanediol is conducted by hydrolyzing the optically active fluoroalkyl ethylene oxide, which has been obtained by the reaction, without an isolation thereof.

[Invention 16]

An optically active 1-chloro-3,3-difluoroisopropyl alcohol represented by formula:

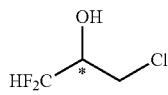

[In the formula, * represents an asymmetric atom.].

[Invention 17]

An optically active 2-difluoromethyl ethylene oxide represented by formula:

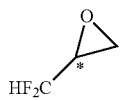

[In the formula, * represents an asymmetric atom.].

The present inventors have eagerly conducted screening of biocatalysts capable of achieving an object of the present invention, among biocatalysts such as microorganism bacterial cells and enzymes. As a result, we have found a biocatalyst providing optically active fluoroalkyl chloromethyl alcohol that is highly convenient as an intermediate of optically active fluoroalkyl ethylene oxide, thereby completing the present invention.

Furthermore, during its process, the present inventors have obtained very useful findings that both optical isomers of optically active fluoroalkyl chloromethyl alcohol can be made separately by changing the biocatalyst to be used.

In the present invention, fluoroalkyl bromomethyl ketone represented by formula [5]

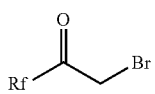

[5]

was also cited as a candidate for the substrate of biocatalysts. It was, however, confirmed that a method using biocatalyst requires water as solvent, and bromine atom in the compound is released in water, thereby not obtaining the target optically active fluoroalkyl bromo alcohol (see the after-mentioned Comparative Example). Like this, based on findings that fluoroalkyl bromomethyl ketone cannot be used in a method using biocatalyst, it was decided in the present invention to use the above compound with a chlorine atom introduced, which is stable even in the presence of water.

The concentration of the fluoroalkyl chloromethyl ketone means the concentration (w/v) of the ketone in the reaction liquid (concentration of the reduced product is not considered (is omitted) and does not determine the total amount of the ketone added throughout the reaction.

The optically active fluoroalkyl chloromethyl alcohol formed in the reaction liquid can be collected by distillation, extraction, etc. By treating the alcohol with base, it can be converted into an optically active fluoroalkyl ethylene oxide while maintaining optical purity. Furthermore, the optically active fluoroalkyl ethylene oxide can be converted by hydrolysis into an optically active fluoroalkyl-1,2-ethanediol while maintaining optical purity.

Hitherto, there have not been known findings like the present invention that a biocatalyst for providing an optically active fluoroalkyl chloromethyl alcohol with a high optical purity is found, and both optical isomers of optically active fluoroalkyl chloromethyl alcohol are efficiently produced, followed by conversion into the optically active fluoroalkyl ethylene oxide while maintaining optical purity.

In particular, with respect to the substrate as one target in the present invention where Rf has a difluoromethyl group, it is extremely difficult to conduct an asymmetric reduction of the fluoroalkyl chloromethyl ketone by ordinary chemical procedures. Therefore, it was not possible to obtain an optically active fluoroalkyl chloromethyl alcohol of high optical purity by conventional techniques (see Reference Example 1).

Optically active 2-difluoromethyl ethylene oxide (the case in which Rf of optically active fluoroalkyl ethylene oxide represented by formula [3] is a difluoromethyl group) and its precursor, optically active 1-chloro-3,3-difluoroisopropyl alcohol (the case in which Rf of optically active fluoroalkyl chloromethyl alcohol represented by formula [2] is a difluoromethyl group), are novel compounds.

Advantageous Effect of the Invention

According to the present invention, it is possible to efficiently produce an optically active fluoroalkyl ethylene oxide that is important as an intermediate of medicines and agricultural chemicals.

It is possible to obtain a biocatalyst that provides an optically active fluoroalkyl chloromethyl alcohol as a precursor of the ethylene oxide, by a screening using a fluoroalkyl chloromethyl ketone hydrate as the substrate. By further conducting an asymmetric reduction (a method of conducting regeneration by a dehydrogenase without newly adding coenzyme NAD(P)H from outside), it is possible to obtain an optically active fluoroalkyl chloromethyl alcohol with a productivity industrially adaptable.

MODE FOR IMPLEMENTING THE INVENTION

In the following, the present invention is explained in detail. The scope of the present invention is not restricted by these explanations. Besides the following exemplification, it can be conducted with suitable modifications to the extent that the gist of the present invention is not spoiled.

The present invention provides a production method (referred to as Step 1 in the description) for obtaining an optically active fluoroalkyl chloromethyl alcohol represented by formula [2] by treating a fluoroalkyl chloromethyl ketone represented by formula [1] with a microorganism having an activity for asymmetrically reducing the ketone or an enzyme having the activity, and a production method (referred to as Step 2 in the description) for obtaining an optically active fluoroalkyl ethylene oxide represented by formula [3] by treating an optically active fluoroalkyl chloromethyl alcohol, which has been produced by the method of Step 1, with base to achieve a ring closure reaction.

Furthermore, including a production method (referred to as Step 3 in the description) for obtaining an optically active fluoroalkyl-1,2-ethanediol represented by formula [4] by hydrolyzing the optically active fluoroalkyl ethylene oxide, which has been produced by the method of Step 2, to achieve a ring opening reaction, they are summarized as scheme in the following.

[Step 1]

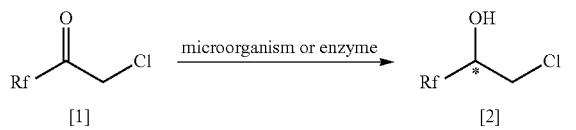

[Step 2]

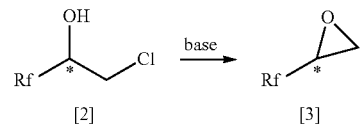

[Step 3]

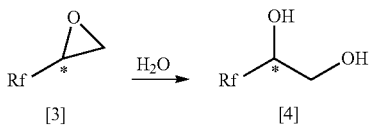

In the formulas, Rf is $C_{1-6}$ straight-chain or branched chain fluoroalkyl group, and * represents an asymmetric atom.

[Step 1]

Step 1 is explained. A fluoroalkyl chloromethyl ketone represented by formula [1] is a publicly known compound. It may suitably be prepared by a person skilled in the art, based on prior art, or a commercial product may be used.

Of a fluoroalkyl chloromethyl ketone represented by formula [1], Rf is a $C_{1-6}$ straight-chain or branched chain fluoroalkyl group having at least one fluorine atom. As specific structures, it is possible to cite trifluoromethyl group, pentafluoroethyl group, heptafluoropropyl group, nonafluorobutyl group, difluoromethyl group, 1,1-difluoroethyl group, 2,2-difluoroethyl group, 1,1-difluoropropyl group, 2,2-difluoropropyl group, 3,3-difluoropropyl group, 1,1-difluorobutyl group, 2,2-difluorobutyl group, 3,3-difluorobutyl group, 4,4-difluorobutyl group, monofluoromethyl group, 1-monofluoroethyl group, 2-monofluoroethyl group, 1-monofluoropropyl group, 2-monofluoropropyl group, 3-monofluoropropyl group, 1-monofluorobutyl group, 2-monofluorobutyl group, 3-monofluorobutyl group, and 4-monofluorobutyl group. Of these, trifluoromethyl group, pentafluoroethyl group, heptafluoropropyl group, nonafluorobutyl group, and difluoromethyl group are preferable, and trifluoromethyl group and difluoromethyl group are particularly preferable.

A major reaction of Step 1 is a reaction for obtaining an optically active fluoroalkyl chloromethyl alcohol represented by formula [2] by treating the fluoroalkyl chloromethyl ketone with a microorganism having an activity for asymmetrically reducing the ketone or an enzyme having the activity. By this reaction, it is possible to obtain an optically active fluoroalkyl chloromethyl alcohol that is highly convenient as an intermediate of an optically active fluoroalkyl ethylene oxide.

As the fluoroalkyl chloromethyl ketone represented by formula [1], as shown in the after-mentioned Examples, a fluoroalkyl chloromethyl ketone hydrate represented by formula [6]:

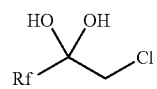

and an alcohol-adduct represented by formula [7]

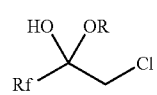

[In formula [6] or formula [7], Rf is defined as in formula [1], and R represents a $C_{1-6}$ straight-chain or branched chain alkyl group] can be also similarly used. Therefore, These hydrate and alcohol adduct are dealt with as being included in claim 1 of the present application.

R in formula [7] represents a $C_{1-6}$ straight-chain or branched chain alkyl group. Specifically, it is possible to cite methyl group, ethyl group, propyl group, isopropyl group, 1-butyl group, 2-butyl group, isobutyl group, tert-butyl group, 1-pentyl group, 2-pentyl group, 3-pentyl group, 2-methyl-1-butyl group, 2-methyl-2-butyl group, 3-methyl-1-butyl group, 3-methyl-2-butyl group, neopentyl group, 1-hexyl group, 2-hexyl group, 3-hexyl group, 2-methyl-1-pentyl group, 3-methyl-1-pentyl group, 4-methyl-1-pentyl group, 2-methyl-2-pentyl group, 3-methyl-2-pentyl group, 4-methyl-2-pentyl group, 2-methyl-3-pentyl group, 3-methyl-3-pentyl group, 2,2-dimethyl-1-butyl group, 2,3-dimethyl-1-butyl group, 3,3-dimethyl-1-butyl group, 2,3-dimethyl-2-butyl group, 3,3-dimethyl-2-butyl group, 2-ethyl-1-butyl group, 1-cyclopropyl group, 1-cyclopentyl group, and 1-cyclohexyl group. Of these, it represents methyl group, ethyl group, propyl group, isopropyl group, 1-butyl group, 2-butyl group, isobutyl group, tert-butyl group, 1-pentyl group, 1-hexyl, or 1-cyclohexyl group. Of these, methyl group, ethyl group, propyl group, isopropyl group, 1-butyl group, isobutyl group, tert-butyl group, and 1-cyclohexyl group are particularly preferable.

The microorganism used here is not particularly limited. It is possible to make a suitable selection from bacteria, yeast, filamentous fungi, etc. For example, it is possible to cite at least one selected from the group consisting of *Cryptococcus curvatus, Pichia farinosa, Torulaspora delbrueckii, Candida cacaoi, Rhodotorula mucilaginosa, Sporidiobolus johnsonii*, and *Trichosporon cutaneum*. Preferably, it is possible to cite at least one selected from the group consisting of *Cryptococcus curvatus, Pichia farinosa, Candida cacaoi*, and *Trichosporon cutaneum*. More preferably, it is possible to cite at least one selected from the group consisting of *Cryptococcus curvatus, Pichia farinosa*, and *Trichosporon cutaneum*. Furthermore, it is possible to similarly use microorganisms belonging to the same biological species as these.

These microorganisms are deposited in National Institute of Technology and Evaluation (2-49-10, Nishihara, Shibuya-ku, Tokyo, 151-0066) through obtaining deposit numbers respectively shown in the following table. These microorganisms may be mutually deposited in other microorganism strains storing organizations and can be similarly used. These microorganisms are laid open to public and easily accessible to a person skilled in the art.

TABLE 2

| Microorganism | Deposit number | Depositary |
| --- | --- | --- |
| Cryptococcus curvatus | NBRC 1159 | National Institute of Technology and Evaluation |
| Pichia farinosa | NBRC 0462 | National Institute of Technology and Evaluation |
| Torulaspora delbrueckii | NBRC 0381 | National Institute of Technology and Evaluation |
| Candida cacaoi | NBRC 10231 | National Institute of Technology and Evaluation |
| Rhodotorula mucilaginosa | NBRC 0001 | National Institute of Technology and Evaluation |
| Sporidibolus johnsonii | NBRC 6903 | National Institute of Technology and Evaluation |
| Trichosporon cutaneum | NBRC 1198 | National Institute of Technology and Evaluation |

As the microorganism used in the present invention, not only it is possible to use cultured bacterial cells as they are, but also it is possible to use bacterial cells crushed by ultrasonic waves or glass beads, bacterial cells immobilized by acrylamide, etc., bacterial cells treated with an organic compound such as acetone or glutaraldehyde, bacterial cells supported on inorganic supports such as alumina, silica, zeolite and diatomaceous earth, and a cell-free extract prepared from the microorganism.

In the case of using bacterial cell of the microorganism, optical purity may become medium (40 to 70% ee) by the effect of an interaction between reductases having contrary stereoselectivities, but it is also possible to obtain an optical purity that is higher than optical purity shown by the original bacterial cells by using the target enzyme after its purification. For example, it suffices to purify enzymes that catalyze the reaction, such as alcohol dehydrogenase (enzyme reversibly reducing ketones) and carbonyl reductase (enzyme irreversibly reducing ketones), from the microorganism providing the above-mentioned optically active compound. In the purification of the enzymes, it is possible to apply a general protein purification method, such as ammonium sulfate fractionation, hydrophobic chromatography, ion-exchange chromatography, and gel filtration chromatography. Furthermore, it is also possible to similarly use a gene recombinant prepared by introducing genes of an enzyme obtained by cloning of the microorganism.

A microorganism obtained by screening can be used as the target of the isolation source of the enzyme. It is possible to obtain an alcohol dehydrogenase or carbonyl reductase, which is usable in the method of the present invention, from the species to which the microorganism belongs, that is, from the microorganism of Tremellaceae, Saccharomycetaceae, Rhodotorula, Sporidibolus or Trichosporonaceae.

As an enzyme usable in the method of the present invention, it is also possible to use a commercial one. It can be selected by conducting a screening using the fluoroalkyl chloromethyl ketone as the substrate. As the commercial enzyme, it is possible to cite, for example, at least one selected from alcohol dehydrogenase (from yeast) of ORIENTAL YEAST CO., LTD., alcohol dehydrogenase (ZM-ADH, from Zymomonas mobilis) of UNITIKA LTD., and Daicel Corporation's Chiralscreen (registered trademark) OH E001 (the same in the following), E004, E007, E008, E039, E048, E052, E073, E077, E085 and E094, preferably E001, E007, E039, E085 and E094, more preferably E001, E039 and E094. Furthermore, it is also possible to similarly use a gene recombinant that expresses the enzyme.

For culture of the microorganism, it is possible to use a culture medium (solid medium or liquid medium) containing nutrient components, generally used for culture of microorganisms. In the case of conducting a reduction reaction of the fluoroalkyl chloromethyl ketone, which is water-soluble, a liquid medium is preferable. In the culture medium, saccharides such as glucose, sucrose, maltose, lactose, fructose, trehalose, mannose, mannitol and dextrose, alcohols such as methanol, ethanol, propanol, butanol, pentanol, hexanol and glycerol, and organic acids such as citric acid, glutamic acid and malic acid are used as carbon source, and ammonia, ammonium salts, amino acids, peptone, polypeptone, casamino acid, urea, yeast extract, malt extract, corn steep liquor, etc. are used as nitrogen source. Furthermore, it is possible to suitably add a culture medium composition, such as other inorganic salts such as potassium dihydrogenphosphate and dipotassium hydrogenphosphate, vitamins such as inositol and nicotinic acid, and trace metals such as iron, copper, magnesium, boron, manganese and molybdenum.

Of these carbon source, nitrogen source and inorganic salts, as to carbon source, it is preferable to add an amount at which the microorganism proliferates sufficiently and at which the proliferation is not inhibited. Normally, 5-80 g, preferably 10-40 g, is added relative to 1 L of the medium. It is also similar as to nitrogen source, and it is preferable to add an amount at which the microorganism proliferates sufficiently and at which the proliferation is not inhibited. Normally, 5-60 g, preferably 10-50 g, is added relative to 1 L of the medium. As to inorganic salts as the nutrient source, it is necessary to add elements necessary for the proliferation of the microorganism, but the proliferation is inhibited in the case of a high concentration. Therefore, normally, 0.001-10 g is added relative to 1 L of the medium. Depending on the microorganism, a plurality of types of these can be combined for the use.

It is necessary to adjust pH of the medium within a range preferable for the proliferation of the microorganism. It is conducted normally at 4.0-10.0, preferably at 6.0-9.0. It is necessary to adjust the temperature range during the culture within a range preferable for the proliferation of the microorganism. It is conducted normally at 10-50° C., preferably at 20-40° C. During the culture, it is necessary to aerate the medium. It is conducted preferably at 0.3-4 vvm (vvm means the amount of aeration relative to the medium volume per minute, and it is an abbreviation of "volume/volume/ minute"), more preferably at 0.5-2 vvm. For the microorganism having a high oxygen demand, it is optional to conduct aeration with an increased oxygen concentration by an oxygen generator, etc. As to an instrument, such as test tube or flask, making it difficult to set the arbitrary amount of aeration, it suffices to set the amount of the medium at 20% or less of the volume of the instrument and attach a ventilation plug such as cotton plug or silicone plug. It is preferable to stir the medium in order to smoothly progress the culture. In the case of a culture tank, it is conducted preferably at 10-100%, more preferably at 20-90%, of the stirring capacity of the apparatus. On the other hand, in the case of a small-size instrument such as test tube or flask, it is better to conduct that by using a shaker. It is conducted preferably at 50-300 rpm, more preferably at 100-280 rpm. It suffices to set the culture time at a time at which proliferation of the microorganism terminates. It is conducted for 6-72 hours, preferably 12-48 hours.

To treat the fluoroalkyl chloromethyl ketone as the substrate with the microorganism, normally, a suspension obtained by culturing the microorganism can be used as it is for the reaction. In case that a component generated during culture has an adverse effect against the reduction reaction, it is optional to once recover the bacterial cells from the culture medium by an operation such as centrifugation, then again prepare a suspension by using the bacterial cells (resting bacterial cells) to be used for the reaction. Furthermore, it is also possible to use various cell extracts for the reaction, such as one obtained by crushing or the like of cells of the cultured microorganism bacterial cells, and enzymes prepared from the cultured microorganism bacterial cells. On the other hand, in the case of treating the fluoroalkyl chloromethyl ketone as the substrate with the enzyme (purified enzyme), it can be conducted in a buffer solution in which the enzyme is dissolved. Since the present reaction is a reduction reaction, a weakly acid buffer solution is preferable. It is possible to cite a sodium phosphate buffer solution, a potassium phosphate buffer solution, a sodium citrate buffer solution, a potassium citrate buffer solution, a sodium acetate buffer solution, and a potassium acetate buffer solution.

To make the reaction using the microorganism progress efficiently, it is necessary to increase density of the bacterial cells in these suspensions. If density is too high, the reaction may be inhibited by production of autolytic enzymes, terminal metabolic products, etc. Therefore, it is conducted normally at $10^6$ to $10^{12}$ cfu/ml (cfu means the number of colonies formed on an agar medium, colony forming units), preferably at 107 to $10^{11}$ cfu/ml, more preferably at $10^8$ to $10^{10}$ cfu/ml. On the other hand, to make the reaction using the enzyme progress efficiently, it is necessary to increase concentration of the enzyme in the buffer solution. If the enzyme is used too much, it is not economical. Therefore, it is used preferably in a range of 0.01 to 20 g/L, more preferably in a range of 0.1 to 10 g.

In adding the fluoroalkyl chloromethyl ketone to these suspensions or buffer solutions, it is preferable to maintain concentration of the ketone at a concentration at which the reduction reaction progresses smoothly and there is no adverse effect on the activity of microorganism or enzyme. In case that concentration of the ketone is higher than 20% (w/v), the microorganism may die out or the enzyme may alter. Therefore, it is conducted at a concentration lower than this value, that is, normally at 0.01-15% (w/v), preferably 0.05-10% (w/v). As to the basis of the volume for calculating the ketone concentration, it suffices to consider, for example, the amount of the culture medium introduced into a test tube prior to steam sterilization in the after-mentioned Example 1 or the total amount of the microorganism suspension after culture in the after-mentioned Example 7, as a guide.

As to the temperature (i.e., reaction temperature) when treating the fluoroalkyl chloromethyl ketone as the substrate with the microorganism or enzyme, it is necessary to maintain a range preferable for the microorganism or enzyme. It is normally 5-60° C., preferably 15-50° C., more preferably 15-38° C. Furthermore, as to pH during the treatment (i.e., pH during the reaction) too, it is necessary to maintain a preferable range. It is normally 4.0-8.0, preferably 5.5-8.0, more preferably 5.5-7.0.

When the microorganism suspension or enzyme buffer solution is in a standstill condition, the reaction efficiency lowers. Therefore, the reaction is conducted while stirring the reaction liquid. Although the reaction can be conducted with no aeration, it is optional to conduct aeration according to need. At that time, in case that the amount of aeration is too much, there is a risk that the fluoroalkyl chloromethyl ketone and the optically active fluoroalkyl chloromethyl alcohol would disperse as gas to the outside of the system. Therefore, the amount of aeration is preferably 0.3 vvm or less, more preferably 0.1 vvm or less. It suffices to determine the reaction time depending on the target formation condition. It is normally 6 to 312 hours.

In the present invention, coenzyme NAD(P)H (hydrogen donor), which is used for the reduction reaction, can be regenerated from coenzyme NAD(P) by a coenzyme regeneration enzyme (glucose dehydrogenase, formate dehydrogenase, glycerol dehydrogenase, or alcohol dehydrogenase; it is the same in the following). In the reaction using the microorganism, it is possible to use a coenzyme regeneration enzyme that is originally possessed by the microorganism. As to the recombinant, it is possible to use a coenzyme regeneration enzyme that is expressed by incorporating desired genes. As the substrate of the coenzyme regeneration enzyme, it is necessary to add a substrate corresponding to each enzyme. It is conducted while adding glucose, formic acid, glycerol or alcohol. It is also possible to conduct the reduction reaction by separately adding a commercial product of coenzyme NAD(P)H, but it is not economical due to its very high price. The number of reductions per bacterial cell (enzyme) increases by conducting the regeneration through the coenzyme regeneration enzyme without newly adding coenzyme NAD(P)H from outside, like the present invention. Therefore, it is possible to economically produce the target with a high productivity.

To collect the formed optically active fluoroalkyl chloromethyl alcohol from the reaction-terminated liquid (a mixed liquid containing impurities after the termination of the reaction), it is possible to adopt a general isolation method in organic syntheses, such as distillation, extraction by organic solvent and solid phase extraction. In particular, there is a point that a crude product of the present compound can be easily collected with good yield as aqueous solution by conducting distillation, directly from the reaction-terminated liquid or a filtrate resulting from removing bacterial cells by filtration according to need. This point is useful even if it is compared with prior art. According to need, the obtained crude product's aqueous solution can be subjected to a purification operation such as dehydration, activated carbon, fractional distillation, or column chromatography. A point that the crude product as it is can be directly used for synthesizing the optically active fluoroalkyl ethylene oxide in the next step is also one of preferable modes from the industrial viewpoint.

As a method for purifying the crude product, particularly extraction by organic solvent and the subsequent fractional distillation are preferable. As the organic solvent, it is possible to adopt ether solvents, ester solvents, halogen-containing solvents, aliphatic hydrocarbon solvents, aromatic hydrocarbon solvents, etc. Specifically, it is possible to cite diethyl ether, diisopropyl ether, dibutyl ether, methyl-tert-butyl ether, cyclopentyl methyl ether, tetrahydrofuran, 2-methyltetrahydrofuran, methyl acetate, ethyl acetate, propyl acetate, t-butyl acetate, methylene chloride, chloroform, 1,2-dichloroethane, n-hexane, cyclohexane, n-heptane, n-nonane, n-octane, toluene, xylene, etc. Diethyl ether, diisopropyl ether, methyl-tert-butyl ether, tetrahydrofuran, 2-methyltetrahydrofuran, methyl acetate, ethyl acetate, propyl acetate, methylene chloride, chloroform, 1,2-dichloroethane, n-hexane, cyclohexane, n-heptane, and toluene are preferable. Diethyl ether, diisopropyl ether, methyl-tert-butyl ether, 2-methyltetrahydrofuran, ethyl acetate, methylene chloride, chloroform, n-hexane, and toluene are particularly preferable. These solvents may be used singly or in combination.

Furthermore, it is also possible to collect the optically active fluoroalkyl chloromethyl alcohol by extraction by using the above-mentioned organic solvent directly from a filtrate resulting from removing bacterial cells from the reaction-terminated liquid and then conducting its concentration.

[Step 2]

Next, Step 2 is explained. Step 2 is a step in which the optically active fluoroalkyl chloromethyl alcohol represented by formula [2] and produced by the above step is used as the raw material, and the alcohol is treated with base to obtain the optically active fluoroalkyl ethylene oxide represented by formula [3]. Herein, it is treated with base to achieve a ring closure. With this, it can be converted into the optically active fluoroalkyl ethylene oxide without lowering optical purity.

As the base to be used in the present step, it is possible to cite inorganic base or organic base. As the inorganic base, it is possible to cite alkali metal hydrides, alkali-earth metal hydrides, alkali metal hydroxides, alkali-earth metal hydroxides, alkali metal carbonates, alkali-earth metal carbonates, alkali metal hydrogencarbonates or alkali-earth metal hydrogencarbonates, alkali metal amides, alkali metals, etc.

Of these, alkali metal hydrides, alkali metal hydroxides, alkali metal carbonates, alkali-earth metal carbonates, alkali metal hydrogencarbonates or alkali-earth metal hydrogencarbonates are preferable. Alkali metal hydrides, alkali metal carbonates, alkali-earth metal carbonates or alkali metal hydrogencarbonates are particularly preferable.

Specifically, it is possible to cite lithium hydride, sodium hydride, potassium hydride, rubidium hydride, cesium hydride, magnesium hydride, calcium hydride, lithium hydroxide, sodium hydroxide, potassium hydroxide, rubidium hydroxide, cesium hydroxide, magnesium hydroxide, calcium hydroxide, lithium carbonate, sodium carbonate, potassium carbonate, rubidium carbonate, cesium carbonate, magnesium carbonate, calcium carbonate, lithium hydrogencarbonate, sodium hydrogencarbonate, potassium hydrogencarbonate, rubidium hydrogencarbonate, cesium hydrogencarbonate, magnesium hydrogencarbonate, calcium hydrogencarbonate, sodium amide, potassium amide, sodium, and potassium. Of these, lithium hydride, sodium hydride, potassium hydride, lithium hydroxide, sodium hydroxide, potassium hydroxide, rubidium hydroxide, cesium hydroxide, sodium carbonate, potassium carbonate, rubidium carbonate, cesium carbonate, calcium carbonate, calcium carbonate, sodium hydrogencarbonate, potassium hydrogencarbonate, rubidium hydrogencarbonate, cesium hydrogencarbonate, magnesium hydrogencarbonate, and calcium hydrogencarbonate are preferable. Sodium hydride, potassium hydroxide, potassium carbonate, cesium carbonate, sodium carbonate, calcium carbonate, potassium hydrogencarbonate, and cesium hydrogencarbonate are particularly preferable. These can be used singly by one kind or in combination of at least two kinds.

On the other hand, as the organic base, it is possible to cite pyridines, trialkylamines, N,N-dialkylanilines, etc., but pyridines and trialkylamines are preferable. Specifically, it is possible to cite pyridine, methylpyridine, ethylpyridine, dimethylpyridine, methylethylpyridine, diethylpyridine, trimethylpyridine, dimethylaminopyridine, 2,2'-bipyridyl, 4-dimethylaminopyridine, trimethylamine, triethylamine, tripropylamine, tributylamine, diisopropylethylamine, N,N-dimethylaniline, and N,N-diethylaniline. Of these, pyridine, trimethylamine, triethylamine, tributylamine, and diisopropylethylamine are particularly preferable. These can be used singly by one kind or in combination of at least two kinds. Furthermore, it is also possible to use a combination of at least two of these organic base and inorganic base.

It suffices that the base is used by 0.1 mol or greater, preferably 0.2 to 20 mol, particularly preferably 0.3 to 10 mol, relative to the fluoroalkyl chloromethyl alcohol represented by the general formula [2].

As the reaction solvent, besides water, it is possible to cite aliphatic hydrocarbon series such as n-hexane and n-heptane, aromatic hydrocarbon series such as toluene and xylene, halogenated hydrocarbon series such as methylene chloride and 1,2-dichloroethane, ether series such as diethyl ether, tetrahydrofuran, diisopropyl ether, tetrahydrofuran, tert-butyl methyl ether, 1,2-dimethoxyethane and diglyme, ester series such as ethyl acetate and n-butyl acetate, amide series such as N,N-dimethylformamide and 1,3-dimethyl-2-imidazolidinone, and nitrile series such as acetonitrile and propionitrile, dimethylsulfoxide, etc. Of these, water, n-heptane, toluene, methylene chloride, tetrahydrofuran, 1,2-dimethoxyethane, diglyme, ethyl acetate, N,N-dimethylformamide, acetonitrile, and dimethylsulfoxide are preferable. These reaction solvents can be used singly or in combination. Furthermore, in the present invention, it can also be conducted with no solvent.

It suffices that the reaction solvent is used by 0.01 L or greater, preferably 0.03 to 10 L, particularly preferably 0.05 to 7 L, relative to 1 mol of the fluoroalkyl chloromethyl alcohol represented by the general formula [2].

The reaction time may be 72 hours or shorter. It depends on the raw material substrate and the reaction condition. Therefore, it is preferable to follow the reaction progress condition by an analytical means such as gas chromatography, liquid chromatography, nuclear magnetic resonance, etc. It is preferable to determine the time when the raw material substrate has almost disappeared, as terminal point.

The reaction temperature is preferably in a range of −30 to 120° C., normally preferably −20 to 100° C., particularly more preferably −10 to 80° C. In the present invention, all reagents may be mixed together at the same time to start the reaction. Since it is an exothermic reaction, it is possible to maintain a preferable temperature range by adopting a method of slowly adding base to the fluoroalkyl chloromethyl alcohol under cooling with ice or the opposite dropwise addition method. Therefore, it is one of preferable modes. In case that temperature is too high, the optically active fluoroalkyl ethylene oxide generated in the system would disperse to the outside of the system. Therefore, it suffices to conduct the reaction while collecting that by a condenser.

To collect the obtained optically active fluoroalkyl ethylene oxide from the reaction-terminated liquid (a mixed liquid containing impurities after the termination of the reaction), it is possible to adopt a general isolation method in organic syntheses, such as filtration, distillation and extraction by organic solvent. Herein, in a method of using the optically active fluoroalkyl chloromethyl alcohol collected by a distillation operation in Step 1 as the starting raw material of the present step, impurities are little, and it is possible to suppress side reactions. Therefore, it is one of preferable modes. The solvent upon extraction is preferably one that does not react with the ethylene oxide. It is possible to cite aliphatic hydrocarbon series such as n-heptane and n-hexane, aromatic hydrocarbon series such as benzene and toluene, halogenated hydrocarbon series such as methylene chloride and chloroform, ether series such as diethyl ether and t-butyl methyl ether, and ester series solvents such as ethyl acetate, methyl acetate and butyl acetate, etc. In such isolation methods, there is easy and industrially desirable an operation of taking out the target by conducting a direct distillation of the reaction liquid after removing solid matter by filtration according to need.

[Step 3]

Next, Step 3 is explained. In the present invention, it is possible to obtain the optically active fluoroalkyl ethylene oxide as the target compound by going through Step 1 to Step 2. In the present step, the ethylene oxide is hydrolyzed to make a ring opening. With this, it is possible to easily achieve a conversion into the optically active fluoroalkyl-1,2-ethanediol represented by the following formula [4] as an optically active compound.

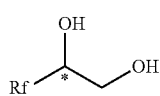

[4]

[In the formula, represents an asymmetrical atom. Rf is defined as in formula [1].]

The ethylene oxide is hydrolyzed to make a ring opening, but the reaction can also be accelerated by adding inorganic base, organic base, inorganic acid or organic acid. As the inorganic base, it is possible to cite alkali metal hydrides, alkali-earth metal hydrides, alkali metal hydroxides, alkali-earth metal hydroxides, alkali metal carbonates, alkali-earth metal carbonates, alkali metal hydrogencarbonates, alkali-earth metal hydrogencarbonates, alkali metal amides, or alkali metals, etc.

Of these, alkali metal hydrides, alkali metal hydroxides, alkali metal carbonates, alkali-earth metal carbonates, alkali metal hydrogencarbonates or alkali-earth metal hydrogencarbonates are preferable. Alkali metal hydrides, alkali metal hydroxides, alkali metal carbonates, alkali-earth metal carbonates or alkali metal hydrogencarbonates are particularly preferable.

Specifically, it is possible to cite lithium hydride, sodium hydride, potassium hydride, rubidium hydride, cesium hydride, magnesium hydride, calcium hydride, lithium hydroxide, sodium hydroxide, potassium hydroxide, rubidium hydroxide, cesium hydroxide, magnesium hydroxide, calcium hydroxide, lithium carbonate, sodium carbonate, potassium carbonate, rubidium carbonate, cesium carbonate, magnesium carbonate, calcium carbonate, lithium hydrogencarbonate, sodium hydrogencarbonate, potassium hydrogencarbonate, rubidium hydrogencarbonate, cesium hydrogencarbonate, magnesium hydrogencarbonate, calcium hydrogencarbonate, sodium amide, potassium amide, sodium, and potassium. Of these, lithium hydride, sodium hydride, potassium hydride, lithium hydroxide, sodium hydroxide, potassium hydroxide, rubidium hydroxide, cesium hydroxide, sodium carbonate, potassium carbonate, rubidium carbonate, cesium carbonate, calcium carbonate, calcium carbonate, sodium hydrogencarbonate, potassium hydrogencarbonate, rubidium hydrogencarbonate, cesium hydrogencarbonate, magnesium hydrogencarbonate, and calcium hydrogencarbonate are preferable. Sodium hydride, potassium hydroxide, calcium hydroxide, potassium carbonate, cesium carbonate, sodium carbonate, calcium carbonate, potassium hydrogencarbonate, and cesium hydrogencarbonate are particularly preferable. These can be used singly by one kind or in combination of at least two kinds.

As the organic base, it is possible to cite pyridines, trialkylamines, N,N-dialkylanilines, etc. Of these, pyridines and trialkylamines are preferable. Specifically, it is possible to cite pyridine, methylpyridine, ethylpyridine, dimethylpyridine (lutidine), methylethylpyridine, diethylpyridine, trimethylpyridine (collidine), dimethylaminopyridine, 2,2'-bipyridyl, 4-dimethylaminopyridine, trimethylamine, triethylamine, tripropylamine, and tributylamine, diisopropylethylamine, N,N-dimethylaniline, or N,N-diethylaniline, etc. Of these, pyridine, trimethylamine, triethylamine, and tributylamine are preferable. These can be used singly by one kind or in combination of at least two kinds. Furthermore, it is also possible to use a combination of at least two of these organic base and inorganic base.

In the case of acid, as the inorganic acid, it is possible to cite hydrochloric acid, sulfuric acid, phosphoric acid, nitric acid, boric acid, etc., and, as the organic acid, it is possible to cite acetic acid, citric acid, formic acid, lactic acid, oxalic acid, tartaric acid, methanesulfonic acid, etc. Of these, hydrochloric acid and sulfuric acid are preferable in terms of easy availability, cost and easy handling. These can be used singly by one kind or in combination of at least two kinds.

It suffices to use the base or acid by 0.01 mol or greater, preferably 0.02 to 20 mol, particularly preferably 0.03 to 10 mol, relative to the fluoroalkyl ethylene oxide represented by the general formula [3].

It suffices to use water by 0.5 mol or greater, preferably 0.7 mol or greater, particularly preferably 0.9 mol or greater, relative to the fluoroalkyl ethylene oxide represented by the general formula [3].

As the reaction solvent, besides water, it is possible to cite aliphatic hydrocarbon series such as n-hexane and n-heptane, aromatic hydrocarbon series such as toluene and xylene, halogenated hydrocarbon series such as methylene chloride, chloroform and 1,2-dichloroethane, ether series such as diethyl ether, tetrahydrofuran, diisopropyl ether, tetrahydrofuran and tert-butyl methyl ether, ester series such as methyl acetate, ethyl acetate and n-butyl acetate, amide series such as N,N-dimethylformamide and 1,3-dimethyl-2-imidazolidinone, and nitrile series such as acetonitrile and propionitrile, dimethylsulfoxide, etc. Of these, n-heptane, toluene, methylene chloride, tetrahydrofuran, ethyl acetate, water, N,N-dimethylformamide, acetonitrile, tetrahydrofuran, tert-butyl methyl ether and dimethylsulfoxide are preferable. These reaction solvents can be used singly or in combination. Furthermore, in the present invention, it can also be conducted with no solvent.

It suffices that the reaction solvent is used by 0.01 L or greater, preferably 0.03 to 10 L, particularly preferably 0.05 to 7 L, relative to 1 mol of the fluoroalkyl ethylene oxide represented by the general formula [3].

The reaction time may be 72 hours or shorter. It depends on the raw material substrate and the reaction condition. Therefore, it is preferable to follow the reaction progress condition by an analytical means such as gas chromatography, liquid chromatography, nuclear magnetic resonance, etc. It is preferable to determine the time when the raw material substrate has almost disappeared, as terminal point.

The reaction temperature is preferably in a range of −30 to 150° C., normally preferably 0 to 120° C., particularly more preferably 10 to 100° C. In the present invention, all reagents may be mixed together at the same time to start the reaction. Similar to Step 2, since this reaction is also an exothermic reaction, it is possible to maintain a preferable temperature range by adopting a method of slowly adding acid or base to the fluoroalkyl ethylene oxide while maintaining the inside temperature at an appropriate temperature or the opposite dropwise addition method. Therefore, it is one of preferable modes.

To collect the obtained optically active fluoroalkyl-1,2-ethanediol from the reaction-terminated liquid (a mixed liquid containing impurities after the termination of the reaction), it is possible to adopt a general isolation method in organic syntheses, such as filtration, distillation and extraction by organic solvent. As the solvent upon extraction, it is possible to cite aliphatic hydrocarbon series such as n-heptane and n-hexane, aromatic hydrocarbon series such as benzene and toluene, halogenated hydrocarbon series such as methylene chloride and chloroform, ether series such as tetrahydrofuran, 2-methyltetrahydrofuran, diethyl ether, t-butyl methyl ether and cyclopentyl methyl ether, ester series solvents such as ethyl acetate, methyl acetate and butyl acetate, alcohol series solvents immiscible with water, such as n-butanol, n-pentanol and n-hexanol, etc. Of these, tetrahydrofuran, 2-methyltetrahydrofuran, diethyl ether, t-butyl methyl ether, cyclopentyl methyl ether, n-butanol and n-pentanol are preferable. In case that water is mixed with the fraction in the case of taking the target out of the extraction liquid or the reaction terminated liquid by vacuum distillation, a method of obtaining the target of high purity by dehydration of the obtained fraction by a Dean-Stark apparatus or the like is one of preferable modes of this step.

By the way, when conducting the present step, it is possible to conduct Step 3 without intermission by not conducting a post-treatment of Step 2. Specifically, it is possible to obtain the optically active fluoroalkyl-1,2-ethanediol by adding a reagent(s) necessary for Step 3 to the reaction-terminated liquid without isolation of the obtained fluoroalkyl ethylene oxide after termination of Step 2.

Furthermore, when conducting Step 2, besides the optically active fluoroalkyl ethylene oxide as the target of Step 2, an optically active fluoroalkyl-1,2-ethanediol (the target of the present step), which is a compound obtained by hydrolysis of the oxide, may be formed in the reaction system.

In this case, if it is an object to produce the optically active fluoroalkyl-1,2-ethanediol in the present step, it is possible to produce the optically active fluoroalkyl-1,2-ethanediol as the target compound of Step 3 by producing a mixture of the optically active fluoroalkyl ethylene oxide and the optically active fluoroalkyl-1,2-ethanediol in Step 2 and then conducting a purification operation (see, for example, the after-mentioned Example 8).

The optically active fluoroalkyl ethylene oxide, which has been separated by this purification operation, can also be separately reused as the starting raw material in Step 3. This is one of preferable embodiments in the present invention.

As the most preferable mode for obtaining the optically active fluoroalkyl-1,2-ethanediol directly from the fluoroalkyl chloromethyl alcohol, it is to use a reagent of organic base or inorganic base at once, which is common in Step 2 and Step 3, in the presence of water. In particular, using an inorganic base makes it possible to achieve an efficient conversion into the optically active fluoroalkyl-1,2-ethanediol. As to the post-treatment too, it is possible to produce the optically active fluoroalkyl-1,2-ethanediol of high purity by similarly conducting the treatment described in Step 3.

In the method of the present invention, it is possible to produce large amounts of the optically active fluoroalkyl chloromethyl alcohol, which is highly convenient as a precursor of the optically active fluoroalkyl ethylene oxide, by using the fluoroalkyl chloromethyl ketone as the starting material and applying preferable reaction condition. Then, the alcohol is treated with base, thereby easily converting into the optically active fluoroalkyl ethylene oxide. It is highly advantageous as an industrial production method.

It can be obtained with 40% ee or greater, particularly preferably 80% ee or greater, as an optical purity that can be practically adopted, too. The present compound is highly reactive and is very useful as an intermediate for synthesizing optically active fluorine-containing organic compounds. Furthermore, it is also possible to improve optical purity of the compound by optical resolution using column chromatography, recrystallization method, etc.

EXAMPLES

Next, Examples are shown in the following, but the present invention is not limited by the following Examples.

Example 1

Results of Microorganism Reactivity Survey (Screening) Against 3-chloro-1,1-difluoro-2-propanone hydrate There was prepared a liquid medium having a composition of 1000 ml of distilled water, 10 g of polypeptone, 5 g of yeast extract, and 10 g of sodium chloride. It was introduced by 5 ml into each test tube ($\phi$ 1.6 cm×15 cm). Each microorganism shown in the following Table 3 was inoculated, followed by conducting a culture at 28° C. and 160 spm for 48 to 72 hours. After termination of the culture, 3-chloro-1,1-difluoro-2-propanone hydrate of 90 wt % and glucose were added to respectively achieve 1.0% wt/v and 0.1 mol/L to conduct a reduction reaction at 28° C. and 160 rpm for 48 hours. Determination of conversion after the reaction was conducted by an internal standard method of $^{19}$F-NMR (in the following, the same in all of the compounds). In determination of optical purity of 1-chloro-3,3-difluoroisopropyl alcohol, ethyl acetate was mixed with the reaction liquid, followed by extracting the alcohol into the organic layer and conducting an analysis by a gas chromatography using the after-mentioned chiral column (in the following, it was the same). Determination results of conversion and optical purity of each microorganism used are shown in Table 3 as follows.

TABLE 3

| | | 1-chloro-3,3-difluoroisopropyl alcohol | | |
|---|---|---|---|---|
| Microorganism | Deposit number | Conversion | Optical purity | Con-figuration |
| Cryptococcus curvatus | NBRC 1159 | 5% | 68.8% ee | R |
| Pichia farinosa | NBRC 0462 | 80% | 59.5% ee | R |
| Torulaspora delbrueckii | NBRC 0381 | 80% | 43.7% ee | R |
| Candida cacaoi | NBRC 10231 | 79% | 53.8% ee | R |
| Rhodotorula mucilaginosa | NBRC 0001 | 57% | 49.4% ee | R |
| Sporidibolus johnsonii | NBRC 6903 | 80% | 48.5% ee | R |
| Trichosporon cutaneum | NBRC 1198 | 90% | 61.8% ee | R |

In this way, it was possible to obtain an optically active 1-chloro-3,3-difluoroisopropyl alcohol by an asymmetrical reduction reaction by using a microorganism. Among bacterial strains used in the present screening, one showed an optical purity as high as 68.8% ee. It is possible to find bacterial strains providing higher optical purities by increasing the width of the screening. Furthermore, it is also possible to isolate an enzyme that provides a high optical purity by purifying an enzyme from a bacterial strain that showed a high stereoselectivity.

Analysis Condition of Optical Purity of Optically Active 1-chloro-3,3-difluoroisopropyl alcohol 1.2 equivalents of acetic anhydride and 1.2 equivalents of pyridine were reacted with 1-chloro-3,3-difluoroisopropyl alcohol, thereby achieving conversion into an acetoxy compound as the analysis sample. Using Cyclosil-B (0.25 mm×30 m×0.25 µm) made by Agilent Technologies Co. as the column of gas chromatography, optical purity was calculated from the area of a peak obtained by analysis condition in which carrier gas was nitrogen, pressure was 163 kPa, column temperature was 60 to 90° C. (1° C./min) to 150° C. (10° C./min), and temperature of vaporizing chamber and detector (FID) was 230° C. Regarding retention time of respective enantiomers, R form was 15.7 min, and S form was 16.4 min. Configuration was determined by treating an optically active 1-chloro-3,3-difluoroisopropyl alcohol with 48% NaOH to achieve conversion into an optically active 2,2-difluoro ethylene oxide, followed by treatment with 20% H$_2$SO$_4$ to achieve conversion into an optically active 3,3-difluoro-1,2-propanediol as a publicly known compound (although mentioned hereinafter, optical purity is maintained).

Comparative Example 1

Microorganism Reactivity Survey (Screening) Against 3-bromo-1,1,1-trifluoro-2-propanone hydrate By a method similar to that of Example 1, reduction reactions of 3-bromo-1,1,1-trifluoro-2-propanone hydrate by microorganisms were conducted, and the results were written in Table 4. The target optically active 1-bromo-3,3,3-trifluoroisopropyl alcohol was not formed. As the compounds after the reaction were identified, they were 1,1,1-trifluoro-3-hydroxy-2-propanone and 3,3,3-trifluoro-1,2-propanediol. Since a bromine atom of the present compound is released in water, it was found not to be usable as the substrate by a biocatalyst.

A method for measuring optical purity of an optically active compound, which has been chemically prepared, is described hereinafter.

TABLE 4

| Microorganism | Deposit Number | 1-bromo-3,3,3-trifluoroisopropyl alcohol | | |
|---|---|---|---|---|
| | | Conversion | Optical purity | Configuration |
| Candida parapsilosis | NBRC 0708 | Decomposed | Not determined | Not determined |
| Cryptococcus laurentii | NBRC 0609 | Decomposed | Not determined | Not determined |
| Candida viswanathii | NBRC 10321 | Decomposed | Not determined | Not determined |
| Cryptococcus curvatus | NBRC 1159 | Decomposed | Not determined | Not determined |
| Ogataea polymorpha | NBRC 0799 | Decomposed | Not determined | Not determined |
| Wickerhamomyces anomalus | NBRC 0118 | Decomposed | Not determined | Not determined |
| Pichia farinosa | NBRC 0462 | Decomposed | Not determined | Not determined |
| Pichia haplophila | NBRC 0947 | Decomposed | Not determined | Not determined |
| Torulaspora delbrueckii | NBRC 0381 | Decomposed | Not determined | Not determined |
| Ogataea minuta var. minuta | NBRC 0975 | Decomposed | Not determined | Not determined |
| Zygosaccharomyces bailii | NBRC 0493 | Decomposed | Not determined | Not determined |
| Candida guilliermondii | NBRC 10279 | Decomposed | Not determined | Not determined |
| Debaryomyces maramus | NBRC 0668 | Decomposed | Not determined | Not determined |
| Kluyveromyces marxianus | NBRC 10005 | Decomposed | Not determined | Not determined |
| Rhodotorula mucilaginosa | NBRC 0001 | Decomposed | Not determined | Not determined |
| Wickerhamomyces subpeliculosa | NBRC 0198 | Decomposed | Not determined | Not determined |

Analysis Condition of Optical Purity of Optically Active 1-bromo-3,3-trifluoroisopropyl alcohol 1.2 equivalents of trifluoroacetic anhydride and 1.2 equivalents of pyridine were reacted with 1-bromo-3,3,3-trifluoroisopropyl alcohol, thereby achieving conversion into a trifluoroacetoxy compound as the analysis sample. Using BGB-174 (0.25 mm×30 m×0.25 m) made by BGB Analytik AG Co. as the column of gas chromatography, optical purity was calculated from the area of a peak obtained by analysis condition in which carrier gas was nitrogen, pressure was 163 kPa, column temperature was 60 to 90° C. (1° C./min) to 150° C. (10° C./min), and temperature of vaporizing chamber and detector (FID) was 230° C. Regarding retention time of respective enantiomers, R form was 12.9 min, and S form was 13.2 min.

Example 2

[Rough Purification of Enzyme from *Pichia farinosa* NBRC 0462 Bacterial Strain]

A preliminary culture of *Pichia farinosa* NBRC 0462 bacterial strain was conducted in a 5 ml liquid medium prepared in a test tube (φ1.6 cm×15 cm) and having a composition of 1000 ml distilled water, 10 g polypeptone, 5 g yeast extract, and 10 g sodium chloride. This cultured liquid was added to a liquid medium after a high pressure steam sterilization. This liquid medium had a composition of 2500 ml distilled water, 25 g glucose, 12.5 g peptone, 7.5 g yeast extract, 7.5 g malt extract, 7.5 g potassium dihydrogenphosphate and 5.0 g dipotassium hydrogenphosphate and was prepared in a 5 L volume culture tank (made by B.E. Marubishi Co., Ltd., MDN type 5 L(S)). It was cultured at a temperature of 30° C., an aeration of 1.25 L/min, and a stirring blade rotation speed of 400 rpm. During culture, pH was adjusted to 6.5 by using 42.5% phosphoric acid and 14% aqueous ammonia. A cultured liquid after culture was collected, and the bacterial cells were collected by centrifugation using a 500 ml volume centrifuge tube. To the collected bacterial cells, 100 ml of a 0.2 M phosphoric acid buffer solution of pH 7.0 was added to prepare a suspension. Using a beads-type cell-crushing apparatus (made by Bio-Spec Co., BEAD-BEATER), cells in the suspension were crashed. After removing glass beads, there was conducted a centrifugation of 20,000×g, for 30 minutes to prepare a cell-free extract. To 1 ml of this cell-free extract, 1% wt/v of 3-chloro-1,1-difluoro-2-propanone hydrate and 250 μL of 2M glucose were added, and a reduction reaction was conducted at 30° C. for 24 hours. After the reaction, conversion was 100%, and optical purity was 62.0% ee (R).

Example 3

Results of Survey (Screening) of Reactivity of a Commercial Alcohol Dehydrogenase Against 3-chloro-1,1,1-trifluoro-2-propanone hydrate and 3-chloro-1,1-difluoro-2-propanone hydrate To 1 ml of 200 mM potassium phosphate buffer solution (pH 6.5, 206 mM sodium formate, 222 mM glucose, 5 mM NAD$^+$, (NAD$^+$: nicotinamide adenine dinucleotide oxidized type, it is the same in the following), and 5 mM NADP$^+$ (NAD$^+$: nicotinamide adenine dinucleotide phosphoric acid oxidized type, it is the same in the following), 3-chloro-1,1,1-trifluoro-2-propanone hydrate or 3-chloro-1,1-difluoro-2-propanone was added to make 1 weight %. Then, 5 mg of each of Daicel Corporation's Chiralscreen (registered trademark) OH (alcohol dehydrogenase) as shown in "enzyme name" of Table 5 and Table 6 in the following. Then, a reaction was conducted at 25° C. for two days while it was stirred with a magnetic stirrer. Optical purity of 1-chloro-3,3,3-trifluoroisopropyl alcohol was measured by a gas chromatography using the after-mentioned chiral column after extraction with ethyl acetate. Their respective conversions and optical purities after the reaction were measured and are respectively shown in the following Table 5 and Table 6. Optical purity of optically active 1-chloro-3,3,3-trifluoroisopropyl alcohol was analyzed under the after-mentioned analysis condition, after conversion into optically active 2-trifluoromethyl ethylene oxide.

TABLE 5

| | 1-chloro-3,3,3-trifluoroisopropyl alcohol | | |
|---|---|---|---|
| Enzyme name | Conversion | Optical purity | Configuration |
| E001 | 4% | 56.1% ee | R |
| E004 | 1% | 72.8% ee | S |
| E007 | 80% | 80.8% ee | S |
| E008 | 20% | 74.5% ee | S |
| E039 | 100% | 86.5% ee | R |
| E048 | 14% | 75.7% ee | S |
| E073 | 4% | 52.6% ee | S |
| E077 | 5% | 74.1% ee | R |
| E085 | 1% | 77.8% ee | R |
| E094 | 69% | 88.1% ee | R |

TABLE 6

| | 1-chloro-3,3,3-trifluoroisopropyl alcohol | | |
|---|---|---|---|
| Enzyme name | Conversion | Optical purity | Configuration |
| E001 | 53% | 92.8% ee | S |
| E002 | 100% | 46.4% ee | R |
| E007 | 100% | 55.3% ee | R |
| E008 | 55% | 47.1% ee | R |
| E039 | 100% | 85.0% ee | R |

TABLE 6-continued

| | 1-chloro-3,3,3-trifluoroisopropyl alcohol | | |
|---|---|---|---|
| Enzyme name | Conversion | Optical purity | Configuration |
| E052 | 34% | 76.2% ee | R |
| E085 | 28% | 67.3% ee | S |
| E094 | 100% | 91.2% ee | S |

In this manner, even in the case of using purified enzymes, it is possible to obtain the target optically active compounds. By widening the range of screening, it is also possible to file purified enzymes providing higher optical purities.

Analysis Condition of Optical Purity of Optically Active 1-chloro-3,3,3-trifluoroisopropyl alcohol 1.2 equivalents of trifluoroacetic anhydride and 1.2 equivalents of pyridine were reacted with 1-chloro-3,3,3-trifluoroisopropyl alcohol, thereby achieving conversion into a trifluoroacetoxy compound as the analysis sample. Using BGB-174 (0.25 mm×30 m×0.25 m) made by BGB Analytik AG Co. as the column of gas chromatography, optical purity was calculated from the area of a peak obtained by analysis condition in which carrier gas was nitrogen, pressure was 163 kPa, column temperature was 60 to 90° C. (1° C./min) to 150° C. (10° C./min), and temperature of vaporizing chamber and detector (FID) was 230° C. Regarding retention time of respective enantiomers, R form was 13.4 min, and S form was 13.7 min.

Comparative Example 2

By a method similar to that of Example 3, there were evaluated reactivities of Daicel Corporation's Chiralscreen (registered trademark) OH (alcohol dehydrogenase) as shown in "enzyme name" of Table 7 and Table 8 against 3-chloro-1,1,1-trifluoro-2-propanone hydrate or 3-chloro-1,1-difluoro-2-propanone hydrate, and the respective results are shown in the following Table 7 and Table 8.

TABLE 7

| | 1-chloro-3,3,3-trifluoroisopropyl alcohol | | |
|---|---|---|---|
| Enzyme name | Conversion | Optical purity | Configuration |
| E078 | 1% | 1.9% ee | R |
| E079 | 0% | Not determined | Not determined |
| E092 | 0% | Not determined | Not determined |

TABLE 8

| | 1-chloro-3,3-difluoroisopropyl alcohol | | |
|---|---|---|---|
| Enzyme name | Conversion | Optical purity | Configuration |
| E004 | 0% | Not determined | Not determined |
| E031 | 100% | 10.4% ee | S |
| E048 | 0% | Not determined | Not determined |
| E073 | 43% | 17.3% ee | S |
| E077 | 0% | Not determined | Not determined |
| E078 | 0% | Not determined | Not determined |
| E092 | 0% | Not determined | Not determined |

Example 4

Production of (R)-1-chloro-3,3-difluoroisopropyl alcohol by a Gene Recombinant *E. coli* Expressing Alcohol Dehydrogenase As a medium of preliminary culture, a liquid medium having a composition of 1000 ml distilled water, 10 g polypeptone, 5 g yeast extract and 10 g sodium chloride was prepared and introduced into test tubes (φ1.6 cm×15 cm) by 5 ml, followed by steam sterilization at 121° C. for 15 minutes. Into this liquid medium, a gene recombinant *E. coli* expressing a large amount of an alcohol dehydrogenase of Daicel Corporation's Chiralscreen (registered trademark) OH E039 was aseptically inoculated with a platinum loop, followed by culture at 30° C. and 160 spm for one night, thereby obtaining a preliminary culture liquid having an optical density (OD600) of 8.2 at a wavelength of 600 nm.

As a culture medium of main culture, a liquid medium prepared by adding yeast extract, sodium glutamate, glucose, lactose, inorganic salts and a defoaming agent to 2500 ml of distilled water was prepared, followed by putting into a 5 L volume culture tank (made by B.E. Marubishi Co., Ltd., MDN type 5 L(S)) and then steam sterilization at 121° C. for 30 minutes. The preliminary culture liquid was aseptically inoculated into this culture tank, followed by culture at 30° C. and an aeration of 0.5 vvm for 40 hours with stirring, thereby preparing a suspension having an optical density (OD600) of 24. During the culture, pH was adjusted to around 7.0 by using 20% sodium carbonate aqueous solution and 42.5% phosphoric acid aqueous solution. After termination of the culture, aeration was changed to 0 vvm, followed by adding 6.25% wt/v (156.25 g, as content 125.0 g, 853 mmol) of 80% wt/wt of 3-chloro-1,1-difluoro-2-propanone hydrate to the cultured liquid. While conducting regeneration of a coenzyme by formate dehydrogenase, the reduction reaction was conducted for 24 hours at 20° C. and a pH of 6.2. Conversion after the reaction was 96%, and optical purity was 83.0% ee (R).

From the cultured liquid after the reaction, 443 g of an aqueous solution containing 80 g (613 mmol) of (R)-1-chloro-3,3-difluoroisopropyl alcohol was collected by vacuum distillation (inside pressure: 19.2 kPa; steam temperature: 57-61° C.). Yield became 72%.

Example 5

Production of (S)-2-difluoromethyl ethylene oxide

Apart (166 g) of the (R)-1-chloro-3,3-difluoroisopropyl alcohol aqueous solution collected in Example 4 was taken out to adjust the content of the alcohol to 30 g (230 mmol). While cooling with ice, 1.0 equivalent of 48% sodium hydroxide aqueous solution was added dropwise. While checking the inside temperature, the dropwise addition was conducted to maintain 0-3° C. After the dropwise addition, it was stirred at 1° C. for 120 minutes to conduct a ring closure reaction. After the reaction, drawing out was conducted by distillation at a steam temperature of 50-70° C. (atmospheric pressure) to collect 17 g (182 mmol) of (S)-2-difluoromethyl ethylene oxide. By an analysis under the after-mentioned analysis condition, its optical purity was found to be 83.1% ee. Yield was 79%.

Analysis Condition of Optical Purity of Optically Active 2-difluoromethyl ethylene oxide 1.1 equivalents of 2-naphthalene thiol and 1.1 equivalents of triethylamine were added to 2-difluoromethyl ethylene oxide, thereby achieving conversion into a sulfide as the analysis sample. Using Daicel Corporation's CHIRALCEL OD-H (4.6 mm×25 cm, particle size: 5 μm) as a column of high performance liquid chromatography, optical purity was calculated by the peak area obtained by condition that mobile phase was hexane/IPA=95/5, flow rate was 0.7 ml, column temperature was 15° C., and detection wavelength was 230 nm. The retention times of their respective enantiomers were 24.2 min in R form and 27.4 min in S form.

Example 6

Production of (S)-3,3-difluoro-1,2-propanediol

To 17 g (182 mmol) of (S)-2-difluoromethyl ethylene oxide obtained in Example 5, 0.2 equivalents of 20% sulfuric acid aqueous solution was added, followed by stirring at 50° C. for 8 hours. After the reaction, pH of the solution was adjusted to 5 by sodium hydroxide. After removing inorganic salts by filtration, drawing out was conducted by vacuum distillation (inside pressure: 1.5 kPa; steam temperature: 80-81° C.). As water content of the obtained fraction was measured, it was 4.2%. Here, 20 ml of toluene was added, and reflux dehydration was conducted for 5 hours by using a Dean-Stark apparatus. As the residue was separated into two layers of the product and toluene, toluene was separated, thereby obtaining 17 g (152 mmol) of (S)-3,3-difluoro-1,2-propanediol. As optical purity was analyzed under the after-mentioned analysis condition, it was 83.1% ee. The value of water content was 0.3%, and yield was 84%.

Analysis Condition of Optical Purity of Optically Active 3,3-difluoro-1,2-propanediol 2.5 equivalents of acetic anhydride and 2.5 equivalents of pyridine were reacted with 3,3-difluoro-1,2-propanediol, thereby achieving conversion into a diacetoxy compound as the analysis sample. Using Cyclosil-B (0.25 mm×30 m×0.25 μm) made by Agilent Technologies Co. as the column of gas chromatography, optical purity was calculated from the area of a peak obtained by analysis condition in which carrier gas was nitrogen, pressure was 163 kPa, column temperature was 50° C. (5 min), 50-150° C. (5° C./min) and 150° C. (15 min), and temperature of vaporizing chamber and detector (FID) was 230° C. Retention times of their respective enantiomers were 16.3 min in R form and 17.2 min in S form. Steric configurations were determined, based publicly known information.

Example 7

Production of (S)-3,3-difluoro-1,2-propanediol

A part (139 g) of the aqueous solution containing (R)-1-chloro-3,3-difluoroisopropyl alcohol prepared in Example 4 was taken out to adjust the content of the alcohol to 25 g (192 mmol). While cooling with ice, 1.0 equivalent of 48% sodium hydroxide aqueous solution was added dropwise. While checking the inside temperature, the dropwise addition was conducted to maintain 0-3° C. After the dropwise addition, it was stirred at 1° C. for 120 minutes. After that, extraction with 30 mL of 2-methyltetrahydrofuran was conducted three times, thereby obtaining a 2-methyltetrahydrofuran solution containing 14 g of (S)-2-difluoromethyl ethylene oxide. To this solution, 0.2 equivalents of 20% sulfuric acid aqueous solution was added, followed by stirring at 60° C. for 7 hours.

After the reaction, pH of the solution was adjusted to 5 by sodium hydroxide, followed by removing inorganic salts by filtration and then vacuum distillation (inside pressure: 1.5 kPa; steam temperature: 80-81° C.), thereby obtaining 14 g (125 mmol) of(S)-3,3-difluoro-1,2-propanediol. As optical purity was analyzed under the above-mentioned analysis condition, it was 83.2% ee. Yield was 65%.

Example 8

Production of (S)-3,3-difluoro-1,2-propanediol

While the aqueous solution (72 g) containing 13 g (100 mmol) of (R)-1-chloro-3,3-difluoroisopropyl alcohol prepared in Example 4 was cooled with ice, 1.5 equivalents of 48% sodium hydroxide aqueous solution was added dropwise. While checking the inside temperature, the dropwise addition was conducted to maintain 0-3° C. After the dropwise addition, it was stirred at 1° C. for 120 minutes. With this, the ratio of (S)-2-difluoromethyl ethylene oxide as the product to (S)-3,3-difluoro-1,2-propanediol became 21:79. After the reaction, the product was extracted by methyl tert-butyl ether, followed by vacuum distillation, thereby obtaining 4 g (36 mmol) of (S)-3,3-difluoro-1,2-propanediol. Yield became 36%.

Furthermore, as optical purity was analyzed under the above-mentioned analysis condition, it was 83.0% ee.

Example 9

Production of (S)-2-trifluoromethyl ethylene oxide

By treating 3-chloro-1,1,1-trifluoro-2-propanone hydrate with *Trichosporon cutaneum* NBRC 1198 bacterial strain under the above-mentioned screening condition, it was confirmed to provide (R)-1-chloro-3,3,3-trifluoroisopropyl alcohol of 61.0% ee.

There was prepared a liquid medium having a composition of 2000 ml ion exchanged water, 60 g glucose, 30 g peptone, 50 g yeast extract, 4.8 g potassium dihydrogenphosphate and 2.5 g dipotassium hydrogenphosphate, followed by putting into a 5 L volume fermentation tank (made by B.E. Marubishi Co., Ltd., MDN type 5 L(S)) and then steam sterilization at 121° C. for 60 minutes. Into this liquid medium, there was inoculated 50 ml of a $2.0 \times 10^9$ cfu/ml suspension of *Trichosporon cutaneum* NBRC 1198 bacterial strain (optical purity was separately evaluated, 61.5% ee) resulting from a preliminary culture in a 300 ml volume baffled Erlenmeyer flask into which 50 ml of a liquid medium having the same composition had been introduced, followed by culture for 24 hours at 30° C. with an aeration of 1 vvm and a stirring blade rotational speed of 500 rpm, thereby preparing a $5.2 \times 10^9$ cfu/ml (as wet bacterial weight, 92 g/L) suspension. Upon this, pH was adjusted to 6.5 by using 20% wt/wt sodium carbonate aqueous solution. After termination of the culture, aeration was stopped, and the stirring blade rotational speed was changed to 50 rpm. One prepared by hydrating and dissolving 125 g (853 mmol) of 3-chloro-1,1,1-trifluoro-2-propanone and 200 g of glucose in 300 ml of ion exchanged water prepared in another container was automatically added to the suspension by a computer program in a manner to maintain glucose concentration at 2% by using an on-line sugar concentration sensor (on-line biosensor BF-410, made by Biott Corporation).

Reduction of the substrate by the microorganism was monitored at 24-hour intervals. After confirming that conversion became 86.3% at a time of 144 hours later, the reaction was terminated.

In order to collect (R)-1-chloro-3,3,3-trifluoroisopropyl alcohol formed from the reaction liquid after the reaction, distillation was conducted under vacuum condition. 588 ml of the distillate was collected. It was confirmed by internal standard method of $^{19}$F-NMR to contain 54.5 g (367 mmol) of (R)-1-chloro-3,3,3-trifluoroisopropyl alcohol in the aqueous solution. Optical purity was measured by the above-mentioned analysis condition, and it was 60.9% ee (R form). Yield became 43%.

While this aqueous solution containing (R)-1-chloro-3,3,3-trifluoroisopropyl alcohol was cooled with ice, 1.5 equivalents of 48% sodium hydroxide aqueous solution was added dropwise. The dropwise addition was conducted to maintain 0° C., while checking the inside temperature. After the dropwise addition, stirring was conducted at 0° C. for 120 minutes to achieve the ring closure reaction. After the reaction, extraction was conducted by 2-methyltetrahydrofuran. By concentrating the organic layer with a rotary evaporator, 39 g of the formed (S)-2-trifluoromethyl ethylene oxide was collected. As optical purity was analyzed under the after-mentioned analysis condition, it was 60.8% ee (S). It was contained by 23 g (206 mmol), and yield became 56%.

Analysis Condition of Optical Purity of Optically Active 2-trifluoromethyl ethylene oxide by a High Performance Liquid Chromatography Using a Chiral Column 1.1 equivalents of 2-naphthalene thiol and 1.1 equivalents of triethylamine were added to 2-trifluoromethyl ethylene oxide, thereby achieving conversion into a sulfide as the analysis sample. Using Daicel Corporation's CHIRALCEL OD-H (4.6 mm×25 cm, particle size: 5 µm) as a column of high performance liquid chromatography, optical purity was calculated by the peak area obtained by condition that mobile phase was hexane/IPA=95/5, flow rate was 0.7 ml, column temperature was 15° C., and detection wavelength was 230 nm. The retention times of their respective enantiomers were 16.1 min in R form and 18.2 min in S form.

Example 10

Production of (S)-3,3,3-trifluoro-1,2-propanediol

A part of the (S)-2-trifluoromethyl ethylene oxide solution prepared in Example 9 was taken out to adjust the content of the ethylene oxide to 10 g (89 mmol), followed by adding 0.2 equivalents of 20% sulfuric acid aqueous solution to achieve conversion into (S)-3,3,3-trifluoro-1,2-propanediol. As optical purity of the formed (S)-3,3,3-trifluoro-1,2-propanediol was analyzed under the after-mentioned analyst condition, it was 61.0% ee.

Analysis Condition of Optical Purity of Optically Active 3,3,3-trifluoro-1,2-propanediol 2.5 equivalents of acetic anhydride and 2.5 equivalents of pyridine were reacted with 3,3,3-trifluoro-1,2-propanediol, thereby achieving conversion into an acetoxy compound as the analysis sample. Using Cyclosil-B (0.25 mm×30 m×0.25 m) made by Agilent Technologies Co. as the column of gas chromatography, optical purity was calculated from the area of a peak obtained by analysis condition in which carrier gas was nitrogen, pressure was 163 kPa, column temperature was 50° C. (5 min), 50 to 150° C. (5° C./min) and 150° C. (15 min), and temperature of vaporizing chamber and detector (FID) was 230° C. Regarding retention time of respective enantiomers, R form was 11.3 min, and S form was 12.2 min.

Example 11

Production of (S)-1-chloro-3,3-difluoroisopropyl alcohol by a Gene Recombinant *E. coli* Expressing Alcohol Dehydrogenase As a medium of preliminary culture, a liquid medium having a composition of 1000 ml distilled water, 10 g polypeptone, 5 g yeast extract and 10 g sodium chloride was prepared and introduced into test tubes (ϕ1.6 cm×15 cm) by 5 ml, followed by steam sterilization at 121° C. for 15 minutes. Into this liquid medium, a gene recombinant *E. coli* expressing a large amount of an alcohol dehydrogenase of Daicel Corporation's Chiralscreen (registered trademark) OH E094 was aseptically inoculated with a platinum loop, followed by culture at 30° C. and 160 spm for one night, thereby obtaining a preliminary culture liquid having an optical density (OD600) of 6.4 at a wavelength of 600 nm.

As a culture medium of main culture, a liquid medium prepared by adding yeast extract, sodium glutamate, glucose, lactose, inorganic salts and a defoaming agent to 2500 ml of distilled water was prepared, followed by putting into a 5 L volume culture tank (made by B.E. Marubishi Co., Ltd., MDN type 5 L(S)) and then steam sterilization at 121° C. for 30 minutes. The preliminary culture liquid was aseptically inoculated into this culture tank, followed by culture at 30° C. and an aeration of 0.5 vvm for 40 hours with stirring, thereby preparing a suspension having an optical density (OD600) of 22. During the culture, pH was adjusted to around 7.0 by using 20% sodium carbonate aqueous solution and 42.5% phosphoric acid aqueous solution. After termination of the culture, aeration was changed to 0 vvm, followed by adding 6.25% wt/v (156.25 g, as content 140.6 g, 960 mmol) of 90% wt/wt of 3-chloro-1,1-difluoro-2-propanone hydrate to the cultured liquid. While conducting regeneration of a coenzyme by glucose dehydrogenase, the reduction reaction was conducted for 24 hours at 30° C. and a pH of 6.0. Conversion after the reaction was 99%, and optical purity was 89.2% ee (S).

From the cultured liquid after the reaction, 526 g of an aqueous solution containing 85 g (651 mmol) of (S)-1-chloro-3,3-difluoroisopropyl alcohol was collected by vacuum distillation (inside pressure: 19.2 kPa; steam temperature: 57-61° C.). Yield became 68%.

Example 12

Production of (R)-2-difluoromethyl ethylene oxide

While 85 g of (S)-1-chloro-3,3-difluoroisopropyl alcohol aqueous solution (as content 14 g, 105 mmol) collected in Example 11 was cooled with ice, 1.0 equivalent of 48% sodium hydroxide aqueous solution was added dropwise. The dropwise addition was conducted to maintain 0 to 3° C., while checking the inside temperature. After the dropwise addition, stirring was conducted at 1° C. for 120 min to achieve the ring closure reaction. After the reaction, 49 g of the formed (R)-2-difluoromethyl ethylene oxide was collected by distillation at a steam temperature of 50 to 70° C. (atmospheric pressure). The content of the product was found to be 8 g (85 mmol) by an internal standard method of $^{19}$F-NMR. Yield became 81%. As optical purity was analyzed under the above-mentioned analysis condition, it was 89.1% ee.

Example 13

Production of (R)-3,3-difluoro-1,2-propanediol 0.2 equivalents of 20% sulfuric acid aqueous solution was added to 49 g of (R)-2-difluoromethyl ethylene oxide aqueous solution (as content 8 g, 85 mmol) prepared in Example 12, followed by stirring at 60° C. for 7 hours. After the reaction, pH of the solution was adjusted to 5 by sodium hydroxide. After removing inorganic salts by filtration, vacuum distillation (inside pressure: 1.5 kPa; steam temperature: 80 to 81° C.) was conducted, thereby collecting 46 g of (R)-3,3-difluoro-1,2-propanediol solution. The content of the product was found to be 7 g (66 mmol) by an internal standard method of $^{19}$F-NMR, and yield became 78%. Furthermore, as optical purity was analyzed under the above-mentioned analysis condition, it was 89.2% ee.

Example 14

Production of (S)-1-chloro-3,3-difluoroisopropyl alcohol by a Gene Recombinant *E. coli* Expressing Alcohol Dehydrogenase As a medium of preliminary culture, a liquid medium having a composition of 1000 ml distilled water, 10 g polypeptone, 5 g yeast extract and 10 g sodium chloride was prepared and introduced into test tubes (ϕ1.6 cm×15 cm) by 5 ml, followed by steam sterilization at 121° C. for 15 minutes. Into this liquid medium, a gene recombinant *E. coli* expressing a large amount of an alcohol dehydrogenase of Daicel Corporation's Chiralscreen (registered trademark) OH E094 was aseptically inoculated with a platinum loop, followed by culture at 30° C. and 160 spm for one night, thereby obtaining a preliminary culture liquid having an optical density (OD600) of 7.2 at a wavelength of 600 nm.

As a culture medium of main culture, a liquid medium prepared by adding yeast extract, sodium glutamate, glucose, lactose, inorganic salts and a defoaming agent to 2500 ml of distilled water was prepared, followed by putting into a 5 L volume culture tank (made by B.E. Marubishi Co., Ltd., MDN type 5 L(S)) and then steam sterilization at 121° C. for 30 minutes. The preliminary culture liquid was aseptically inoculated into this culture tank, followed by culture at 30° C. and an aeration of 0.5 vvm for 40 hours with stirring, thereby preparing a suspension having an optical density (OD600) of 23. During the culture, pH was adjusted to around 7.0 by using 20% sodium carbonate aqueous solution and 42.5% phosphoric acid aqueous solution. After termination of the culture, aeration was changed to 0 vvm, followed by adding 6.25% wt/v (151.2 g, as content 140.6 g, 960 mmol) of 93% wt/wt of 3-chloro-1,1-difluoro-2-propanone hydrate to the cultured liquid. While conducting regeneration of a coenzyme by glucose dehydrogenase, the reduction reaction was conducted for 24 hours at 30° C. and a pH of 6.0. Conversion after the reaction was 99%, and optical purity was 90.7% ee (S).

After adding calcium chloride dihydrate (36 g) to the cultured liquid after the reaction, 467 g of an aqueous solution containing (S)-1-chloro-3,3-difluoroisopropyl alcohol was collected by vacuum distillation (inside pressure: 19.2 kPa; steam temperature: 57 to 61° C.). To the collected aqueous solution, 450 ml of methyl tert-butyl ether was added, followed by stirring to conduct extraction. It was separated into two layers. 450 ml of methyl tert-butyl ether was added again to the aqueous layer to conduct extraction. Concentration of the combined organic layer was conducted to distill off methyl tert-butyl ether (inside pressure: 23 kPa). The residue became 100 g of 73.5 wt % methyl tert-butyl ether solution containing (S)-1-chloro-3,3-difluoroisopropyl alcohol (74 g, 563 mmol, 90.6% ee). Yield was 59%.

Example 15

Production of (R)-2-difluoromethyl ethylene oxide 9.0 g of 73.5 wt % methyl tert-butyl ether solution of (S)-1-chloro-3,3-difluoroisopropyl alcohol (as content 6.6 g, 0.050 mmol) obtained in Example 14 was added dropwise at room temperature to a solution of potassium carbonate (8.3 g, 0.060 mmol) and diglyme (25 ml). After the dropwise addition, stirring was conducted for 21 hours, while maintaining the inside temperature at 40° C. After the reaction, inorganic salts were removed by vacuum filtration. The filtrate was subjected to vacuum distillation (inside pressure: 43 kPa; steam temperature: 47° C.), thereby obtaining 7.1 g (51.4 wt %, 0.039 mol) of (R)-2-difluoromethyl ethylene oxide with a yield of 78%. As optical purity was analyzed under the above-mentioned analysis condition, it was 90.6% ee.

Example 16

Production of (R)-3,3-difluoro-1,2-propanediol 17.7 g of 73.5 wt % methyl tert-butyl ether solution of (S)-1-chloro-3,3-difluoroisopropyl alcohol (as content 13.0 g, 0.10 mmol) was added dropwise at room temperature to 48 wt % potassium carbonate aqueous solution (37.5 g, 0.13 mmol). As it was, the reaction was conducted for 5 hours in a bath of 60° C. With this, conversion became 99%. After the reaction, it was cooled with ice, followed by vacuum filtration to remove inorganic salts. The filtrate was extracted with 20 ml of THF. The separated aqueous layer was further extracted with 20 ml of THF. The extraction was conducted three times in total. The combined organic layer was subjected to vacuum distillation (inside pressure: 3.0 kPa; steam temperature: 87° C.), thereby obtaining (R)-3,3-difluoro-1,2-propanediol (9.9 g, 0.088 mol, yield: 88%). As purity was measured by gas chromatography, it was 99.3%. As optical purity was analyzed under the above-mentioned analysis condition, it was 90.6% ee.

Reference Example 1

Reduction Reactions of 3-chloro-1,1-difluoro-2-propanone Hydrate Using Chemical Catalysts Under argon gas atmosphere, 20 mL autoclave was charged with a ruthenium complex (0.008 mmol, substrate/catalyst ratio: 700), potassium formate (0.967 g, 11.5 mmol), tetrabutylammonium bromide (TBAB) (0.181 g, 0.56 mmol), water (0.56 mL), formic acid (0.63 mL, 16.7 mmol, 0.3 equivalents relative to the ketone used), and 3-chloro-1,1-difluoro-2-propanone hydrate (5.6 mmol). The container was tightly closed, and stirring was conducted at 30° C. for 21 hours. The measurement results of conversion and optical purity for each ruthenium complex used are shown in the following Table 9.

TABLE 9

| | 1-chloro-3,3-difluoroisopropyl alcohol | | |
|---|---|---|---|
| Ruthenium complex | Conversion (%) | Optical purity (e.e) | Configuration |
| RuCl[S,S)-Tsdpen](mesitylene) | 100 | 2.6 | R |
| RuCl[S,S)-Tsdpen](p-cymene) | 100 | 4.5 | R |
| RuCl[S,S)-Fsdpen](p-cymene) | 100 | 2.8 | R |
| (S,S)-Ts-DENEB | 100 | 9.3 | R |

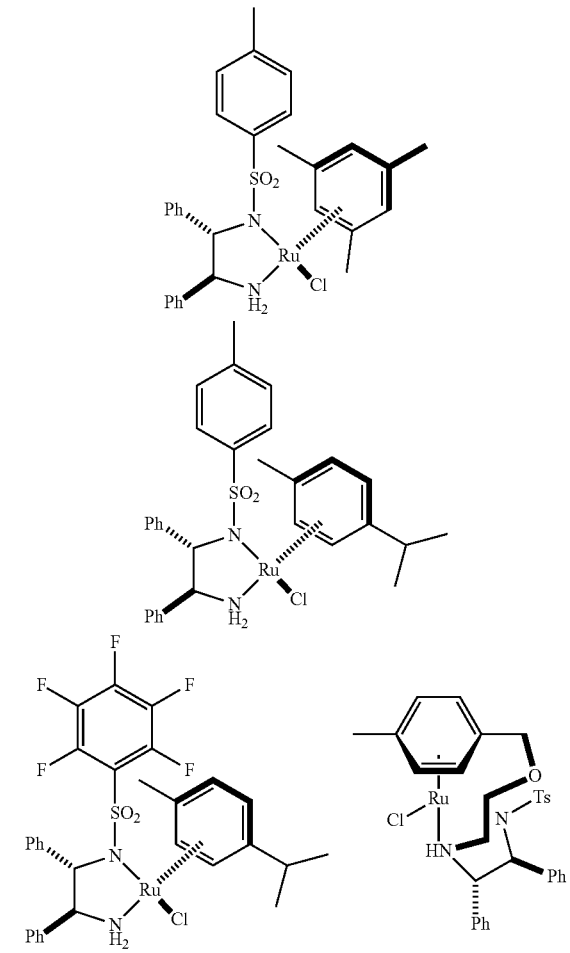

(From the left, the above formulas represent the structures of RuCl[(S,S)-Tsdpen](mesitylene), RuCl[(S,S)-Tsdpen](p-cymene), RuCl[(S,S)-Fsdpen](p-cymene), and (S,S)-Ts-DENEB. Ph represents a phenyl group, and Ts represents a p-toluenesulfonyl group.) Like this, in asymmetrical reduction reactions using chemical catalysts, optical purities of 1-chloro-3,3-difluoroisopropyl alcohol were low.

INDUSTRIAL USABILITY

An optically active fluoroalkyl ethylene oxide, which is the target of the production method of the present invention, can be used as an intermediate of medicines and agricultural chemicals.

The invention claimed is:

1. A method for producing an optically active fluoroalkyl chloromethyl alcohol represented by formula [2]:

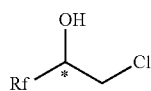

wherein, * represents an asymmetric atom, and Rf is defined as in formula [1],
the method comprising the step of treating a fluoroalkyl chloromethyl ketone represented by formula [1]:

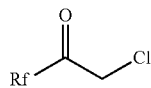

wherein, Rf represents a $C_{1-6}$ straight-chain or branched-chain fluoroalkyl group having at least one fluorine atom,
with a microorganism having an activity for asymmetrically reducing the ketone or an enzyme having the activity.

2. The production method as claimed in claim 1, wherein Rf in the fluoroalkyl chloromethyl ketone represented by formula [1] is a trifluoromethyl ($CF_3$) group or difluoromethyl ($CF_2H$) group.

3. The production method as claimed in claim 1, wherein the microorganism is at least one selected from the group consisting of *Cryptococcus curvatus*, *Pichia farinosa*, *Torulaspora delbrueckii*, *Candida cacaoi*, *Rhodotorula mucilaginosa*, *Sporidibolus johnsonii*, and *Trichosporon cutaneum*.

4. The production method as claimed in claim 3, wherein the microorganism is a microorganism having a deposit number shown in the following table:

| Microorganism | Deposit number | Depositary |
|---|---|---|
| *Cryptococcus curvatus* | NBRC 1159 | National Institute of Technology and Evaluation |
| *Pichia farinosa* | NBRC 0462 | National Institute of Technology and Evaluation |
| *Torulaspora delbrueckii* | NBRC 0381 | National Institute of Technology and Evaluation |
| *Candida cacaoi* | NBRC 10231 | National Institute of Technology and Evaluation |
| *Rhodotorula mucilaginosa* | NBRC 0001 | National Institute of Technology and Evaluation |
| *Sporidibolus johnsonii* | NBRC 6903 | National Institute of Technology and Evaluation |
| *Trichosporon cutaneum* | NBRC 1198 | National Institute of Technology and Evaluation. |

5. The production method as claimed in claim 1, wherein the enzyme is an alcohol dehydrogenase or carbonyl reductase.

6. The production method as claimed in claim 5, wherein the alcohol dehydrogenase or carbonyl reductase is a microorganism of Tremellaceae, Saccharomycetaceae, *Rhodotorula*, *Sporidibolus* or Trichosporonaceae, a substance treated therewith, a culture thereof, and/or an enzyme obtained from the microorganism.

7. The production method as claimed in claim 1, wherein temperature in the reaction is 5 to 60° C.

8. The production method as claimed in claim 1, wherein pH in the reaction is in a range of 4.0 to 8.0.

9. The production method as claimed in claim 1, comprising the step of distilling a mixed liquid containing the optically active fluoroalcohol obtained after terminating the reaction and an impurity is distilled, thereby separating the impurity from the mixed liquid and purifying the optically active fluoroalcohol.

10. A method for producing an optically active fluoroalkyl ethylene oxide represented by formula [3]:

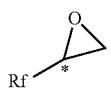

wherein, * represents an asymmetric atom, and Rf represents a $C_{1-6}$ straight-chain or branched-chain fluoroalkyl group having at least one fluorine atom,
wherein the optically active fluoroalkyl chloromethyl alcohol represented by formula [2] is produced by the method of claim 1, and then the alcohol is treated with a base.

11. The production method as claimed in claim 10, wherein the base is at least one selected from the group consisting of alkali metal hydrides, alkali-earth metal hydrides, alkali metal hydroxides, alkali-earth metal hydroxides, alkali metal carbonates, alkali-earth metal carbonates, alkali metal hydrogencarbonates, and alkali-earth metal hydrogencarbonates.

12. The production method as claimed in claim 10, further comprising the step of hydrolyzing the optically active fluoroalkyl ethylene oxide, thereby turning into a fluoroalkyl-1,2-ethanediol represented by formula [4]:

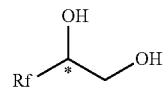

wherein, * represents an asymmetric atom, and Rf represents a $C_{1-6}$ straight-chain or branched-chain fluoroalkyl group having at least one fluorine atom.

13. The method as claimed in claim 12, wherein the hydrolysis is conducted by a treatment with an acid or base.

14. The method as claimed in claim 13, wherein the step of turning into the fluoroalkyl-1,2-ethanediol is conducted in the presence of the base that is at least one basic compound selected from the group consisting of alkali metal hydrides, alkali-earth metal hydrides, alkali metal hydroxides, alkali-earth metal hydroxides, alkali metal carbonates, alkali-earth metal carbonates, alkali metal hydrogencarbonates, and alkali-earth metal hydrogencarbonates.

15. The production method as claimed in claim 12, wherein the step of turning into the fluoroalkyl-1,2-ethanediol is conducted by hydrolyzing the optically active fluoroalkyl ethylene oxide, which has been obtained by the reaction, without an isolation thereof.

16. An optically active 1-chloro-3,3-difluoroisopropyl alcohol represented by formula:

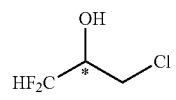
wherein, * represents an asymmetric atom.
* * * * *